(12) United States Patent
Richon

(10) Patent No.: US 10,568,944 B2
(45) Date of Patent: Feb. 25, 2020

(54) TREATMENT OF ROSACEA WITH COMPOSITIONS CONTAINING BROMELAIN

(71) Applicant: Merry Richon, Washington, DC (US)

(72) Inventor: Merry Richon, Washington, DC (US)

(*) Notice: Subject to any disclaimer, the term of this patent is extended or adjusted under 35 U.S.C. 154(b) by 99 days.

(21) Appl. No.: 15/789,018

(22) Filed: Oct. 20, 2017

(65) Prior Publication Data

US 2018/0036390 A1 Feb. 8, 2018

Related U.S. Application Data

(62) Division of application No. 14/632,995, filed on Feb. 26, 2015, now Pat. No. 9,821,040.

(60) Provisional application No. 61/944,904, filed on Feb. 26, 2014.

(51) Int. Cl.
| A61K 38/48 | (2006.01) |
| A61K 9/00 | (2006.01) |
| A61K 47/10 | (2017.01) |
| A61K 47/14 | (2017.01) |
| A61K 47/44 | (2017.01) |

(52) U.S. Cl.
CPC ........ *A61K 38/4873* (2013.01); *A61K 9/0014* (2013.01); *C12Y 304/22032* (2013.01); *C12Y 304/22033* (2013.01); *A61K 47/10* (2013.01); *A61K 47/14* (2013.01); *A61K 47/44* (2013.01)

(58) Field of Classification Search
None
See application file for complete search history.

(56) References Cited

U.S. PATENT DOCUMENTS

| 4,444,751 | A | 4/1984 | Cripps |
| 5,387,517 | A | 2/1995 | Cini |
| 5,441,740 | A | 8/1995 | Ozlen |
| 6,579,543 | B1 | 6/2003 | McClung |
| 6,696,396 | B1 | 2/2004 | Arneson |
| 2003/0026794 | A1* | 2/2003 | Fein .................. A61K 8/66 424/94.2 |
| 2007/0275045 | A1 | 11/2007 | Evans |
| 2012/0104047 | A1 | 5/2012 | Lim |
| 2013/0156745 | A1 | 6/2013 | Hanson |

OTHER PUBLICATIONS

R. Pavan et al., "Properties and Therapeutic Application of Bromelalin: A Review", Biotech. Res. Intl. 2012, article ID 976203.

* cited by examiner

*Primary Examiner* — Michelle F. Paguio Frising

(57) ABSTRACT

Compositions containing bromelain are disclosed for use as topical therapeutic agents for the treatment of rosacea. The compositions include lotions, creams and ointments.

19 Claims, No Drawings

TREATMENT OF ROSACEA WITH COMPOSITIONS CONTAINING BROMELAIN

RELATED APPLICATIONS

This application is a continuation-in-part of U.S. patent application Ser. No. 14/632,995, filed Feb. 26, 2015, now U.S. Pat. No. 9,821,040, which claims priority of U.S. Provisional Patent Application No. 61/944,904 filed on Feb. 26, 2014. The entire contents of both of these applications are incorporated herein by reference.

FIELD OF THE INVENTION

The invention relates to topical compositions for the relief of itching, inflammation, and irritation of the skin, and for the cosmetic improvement of the appearance of skin.

BACKGROUND OF THE INVENTION

1. Itch and Inflammation.

The phenomenon of itching is a widespread source of discomfort and annoyance, and the search for relief has created a significant market for products intended to alleviate the problem. To address this need, a tremendous number of topical products have been released onto the market over the years. These formulations generally contain, in addition to their inert bases, one or more of three classes of active ingredients: anti-histamines, steroids, and anesthetics. There is also available a class of "natural" lotions which utilize components derived from natural sources such as oatmeal and aloe vera; extracts and oils such as menthol, tea oil, and coriander oil; and herbal extracts such as arnica, willow bark, witch hazel and others.

A common home remedy for itch, irritation, and dermal pain is an aqueous paste of meat tenderizer, which is typically applied to insect bites and jellyfish stings to relieve the pain and itch associated with these injuries. The principal ingredient in these products is an enzyme-containing extract from either papaya or pineapple.

The majority of commercially available anti-histamines, steroids, and topical anesthetics are synthetic compounds, which many consumers prefer to avoid if possible. Accordingly, there remains a need for naturally-derived, topical agents capable of safely relieving itch and irritation.

2. Erythema and Inflammation in Allergic and Atopic Dermatitis, Rosacea and Psoriasis.

Rosacea is a chronic condition which is characterized by facial erythema and occasionally red domed papules and pustules. Four subtypes (Phymatous, Erythematotelangiectatic, Papulopustular, and Ocular) and three variants (conglobate, fulminans, and phymatous) of rosacea have been identified. Since there is no specific test for rosacea, it is generally diagnosed by visual inspection and it is currently treated with oral and topical antibiotics, alpha-hydroxy acid peels and dermatological laser treatment (N. Scheinfeld, T. Berk, "A Review of the Diagnosis and Treatment of Rosacea" *Postgraduate Medicine* 2010, 122(1): 139-143; E. J. van Zuuren et al., "Interventions for rosacea" *Cochrane Database of Systematic Reviews* 2015, Issue 4, Art. No. CD003262.) Rosacea has no cure, and lifelong treatment for relief of symptoms is often necessary (B. Culp, N. Scheinfeld, "Rosacea: A Review" *Pharmacy & Therapeutics* 2009, 34(1): 38-45.)

The term "eczema" refers to a set of clinical observations; it is commonly used as a generic term for various forms of dermatitis, including atopic and contact dermatitis. Recent studies have shown that a member of the cathelicidin family of host defense peptides, LL-37, is expressed in small amounts in humans but accumulates in skin affected by diseases such as atopic dermatitis (P. Y. Ong et al., "Endogenous Antimicrobial Peptides and Skin Infections in Atopic Dermatitis" *N Engl. J. Med.* 2002, 347(15): 1151-1160) rosacea (K. Yamasaki et al., "Increased serine protease activity and cathelicidin promotes skin inflammation in rosacea" *Nature Med.* 2007, 13:975-980) and psoriasis. In addition, the IL-19 cytokine is reportedly over-produced in psoriasis patients (E. Witte et al., "IL-19 Is a Component of the Pathogenetic IL-23/IL-17 Cascade in Psoriasis" *J. Invest. Dermatol.* 2014, 134:2757-2767.) Evidence is also mounting for the involvement of mast cells in rosacea (Y. Muto et al., "Mast Cells Are Key Mediators of Cathelicidin-Initiated Skin Inflammation in Rosacea" *J. Invest. Dermatol.* 2014, 134:2728-2736.)

The above-cited studies, and numerous others, have established a connection between dermatological diseases and the over-expression of endogenous peptides. Topical compositions which reduce the amounts of these peptides may therefore provide relief from the symptoms of rosacea, psoriasis, eczema, and related dermatological conditions.

3. Papain and Bromelain.

Papain is a cysteine protease (papaya proteinase I, EC 3.4.22.2) extracted from the unripe fruit of the papaya plant (*Carica papaya*). Bromelain may be either of two broadly-defined cysteine proteases (stem bromelain, EC 3.4.22.32, and fruit bromelain, EC 3.4.22.33) extracted from the plants of the family Bromeliaceae (pineapple.) In commerce, the term may refer to a crude plant extract (a lyophilized, filtered plant juice, acetone powder, or the like) containing both enzymes, although, with most of the fruit being harvested for market, the stem enzyme is most prevalent. Both enzymes are well-known as components of enzymatic compositions for dermal debridement and exfoliation. Their use as oral anti-inflammatory agents has been sporadically described in the literature.

U.S. Pat. No. 3,860,702 discloses a suspension of papain in partially hydrolyzed cocoa butter, useful as a topical anti-inflammatory. Recently, Valeant Pharmaceuticals Australia introduced Stop Itch Plus™, a first aid cream formulated with papain. The product is claimed to relieve itching caused by insect bites, minor burns, cuts, scratches, sunburn and windburn.

U.S. Pat. No. 5,441,740 describes cosmetic compositions containing alpha-hydroxy acids, salicylic acid and mixtures of bromelain and papain for use as dermal exfoliating agents. The compositions are said to be useful for the treatment of skin conditions such as lack of adequate skin firmness, wrinkles, and dry skin. The utility of bromelain for relief from itch and other irritation is not disclosed.

U.S. Patent Application Publication No. 2005/0249720 describes cosmetic formulations of honey and a blend of natural fruits including pineapple, mango, and papaya as active dermal exfoliating agents.

U.S. Pat. Nos. 4,197,291, 4,329,430, 5,387,517, 5,830,739 and 8,119,124 and U.S. Patent Application Publication No. 2013/0156745 also describe bromelain-derived compositions for the enzymatic debridement of burns and wounds.

U.S. Pat. No. 6,579,543 describes topical compositions comprising, among a wide variety of ingredients, at least one compound "having anti-inflammatory activity," and among the many named anti-inflammatory agents is bromelain. The compositions are said to have "analgesic, anti-inflammatory, antioxidant, anti-neuralgic, blood circulation promotion and antidepressant activities," and are allegedly useful for relief from a wide array of "conditions or injuries that cause a subject discomfort," including poison ivy and insect stings and bites.

The U.S. Food and Drug Administration (FDA) in 2008 ordered a halt to the marketing of unapproved drug products that contain papain in a topical dosage form (including Stop Itch Plus™), because the drugs can produce harmful or near-fatal effects, hypersensitivity resulting in anaphylactic reactions being the primary concern. The agency cited cases resulting in cardiovascular symptoms such as hypotension and tachycardia, some requiring emergency rooms visits and treatment with epinephrine. The FDA also asserted that the effectiveness of the products was not supported by scientifically sound studies in the medical literature.

Extracts of *Ananas comosus* (pineapple) stem contain at least eight different proteolytic enzymes (T. Harrach et al., "Isolation and partial characterization of basic proteinases from stem bromelain," 1995, *J. Protein Chem.* 14:41-52.) The crude, unseparated enzyme mixture is commonly referred to as "bromelain". Bromelain has a proteolytic profile that is distinct from that of papain (A. Ritonja et al., "Stem bromelain: amino acid sequence and implications for weak binding of cystatin" 1989, *FEBS Letters* 247:419-424.) Bromelain has long had a variety of reputed uses in folk medicine, and it remains a subject of continual investigation by the alternative medicine community. Numerous bromelain-based "dietary supplements" are marketed for oral consumption, and low levels of bromelain have been incorporated into "natural" cosmetic and analgesic creams and lotions. Non-clinical studies have suggested that bromelain may block proinflammatory metabolites, and that it may affect migration of neutrophils by stripping away cell-surface receptors and ligands. No such effects have ever been confirmed in human studies, however, and with the exception of a burn debridement product (NexoBrid™), bromelain is not approved with a health claim for any disorder by the FDA or by the European Medicines Agency. The U.S. National Institutes of Health rates bromelain as "possibly effective" against osteoarthritis when taken orally, in combination with trypsin and rutin, but no evidence indicates utility or efficacy of bromelain for any other disorder.

SUMMARY OF THE INVENTION

The present invention is directed to compositions for topical application to the skin, which have immediate and long lasting anti-inflammatory, antipruritic and skin-restorative properties. A composition suitable for topical application may be in the form of a liquid, lotion, cream, ointment or gel. When applied topically, the compositions of the invention provide relief of minor skin irritation, discomfort, itch, fissures, and other symptoms caused by a variety of conditions including, but not limited to, psoriasis, seborrhea, eczema, rosacea, allergies, contact and atopic dermatitis, winter itch, dryness-associated fissures in the fingertips and knuckles, insect bites and stings, and the itch associated with diabetes, as well as irritation and itch associated with burns and wound healing, and other conditions or injuries that cause skin discomfort.

According to the present invention, a composition is provided which comprises bromelain dispersed or dissolved in a dermatologically acceptable carrier. The compositions of the invention contain at least about 60 GDU (gelatin dissolving units) of bromelain, and preferably between about 60 and about 300 GDU of bromelain, per gram of composition. Preferred compositions are in the form of lotions or creams, and typically comprise water, emulsifiers, fatty acids, glycerides, and bromelain. The emulsifiers, fatty acids, and glycerides are preferably plant-derived materials.

The present invention also relates to methods for alleviating skin irritation, itch, and inflammation, which comprise applying an effective amount of a composition of the invention to affected areas of the body, as needed for the relief of symptoms.

The compositions disclosed herein provide immediate, long-lasting, and effective relief from the symptoms of chronic conditions such as rosacea, eczema, psoriasis, and various forms of dermatitis, and from minor skin irritations, cuts, insect bites, and stings. The compositions, when so used, have also been observed to restore skin to a more healthy and attractive state.

The compositions of the invention have several advantages over the prior art. For topical application to treat bites and stings, an aqueous paste of meat tenderizer is reportedly effective, if applied as soon as possible after the bite or sting and left on the site of the injury for at least 10 to 15 minutes. As this preparation dries, however, it generally flakes off the site of injury within minutes and therefore has only limited penetration and effectiveness. The specific amount of the active ingredient that actually reaches the targeted tissue is unknown and uncontrolled, and as most meat tenderizers are based on papain, the active ingredient is not usually bromelain. The compositions disclosed herein can be formulated as lotions, creams, or ointments, which remain in place after application and which contain and deliver a consistent concentration of bromelain.

Furthermore, papain has been banned from topical use in the United States by the Food and Drug Association, due to reports of harmful or near-fatal anaphylactic reactions. Bromelain, in contrast, is not known as an allergen or sensitizer. The relative safety of bromelain is indicated by the fact that it is widely sold as a digestive aid, and often marketed with unsupported health claims, without significant side effects being reported. The use of bromelain as a topical therapeutic agent is thus expected to be safer than the use of papain. Compared to papain, bromelain also has a slower and more selective kinetic proteolytic profile, which may reduce the likelihood of undesirable, indiscriminate proteolysis of non-target proteins in the skin.

As used herein, the term "bromelain" refers to an acetone or ethanol powder, or an equivalent crude bromelain extract, derived from the juice of pineapple stem, core and/or fruit. Although bromelain's primary component is a fraction containing cysteine proteases, the commercial bromelain preparations used in the examples herein typically contain peroxidase, phosphatase, and protease-inhibiting activities. The beneficial effects of bromelain that are exploited by the present invention, accordingly, may be due in part to the unique proteases found in bromelain, and may be due in part to additional factors that are not present in papain.

DETAILED DESCRIPTION OF THE INVENTION

Before explaining certain embodiments of the invention in detail by way of exemplary tables, experimentation, results, and laboratory procedures, it is to be understood that the invention is not limited in its application to the details of preparation or to the identities and proportions of the components set forth in the following description or illustrated in the examples, tables, experimentation or results. Those of skill in the art will appreciate that the invention is capable of other embodiments, and of being practiced or carried out in various ways. Also, it is to be understood that the phraseology employed herein is for the purpose of description and should not be regarded as limiting.

The present invention is directed to compositions for topical application to the skin and having immediate and long-lasting antipruritic, anti-inflammatory, and skin-restorative properties. The compositions may be in the form of liquids, lotions, creams, ointments or gels. Topical application of the compositions of the invention provide relief of skin irritation, discomfort, itch and other symptoms caused by a variety of conditions, including but not limited to psoriasis, seborrhea, rosacea, eczema, various allergies, dermatitis, winter itch, chronic itch, cracked fingertips, atopic dermatitis (also known as idiopathic itching), insect bites and stings, fire ant bites, and the itch associated with diabetes, as well as itching and irritation associated with burns, wounds and abrasions that are in the process of healing.

Broadly speaking, the compositions of the invention comprise bromelain dispersed or dissolved in a dermatologically acceptable carrier. The compositions of the invention contain between about 60 and 300 GDU (gelatin dissolving units) of bromelain per gram. Thus, by way of example, if the bromelain employed to prepare a composition of the invention contains 1200 GDU bromelain per gram, suitable compositions will contain between 5 and 25 weight percent of this material. Concentrations of bromelain below about 60 GDU per gram have been found to provide unsatisfactory levels of relief, while concentrations in excess of about 300 GDU bromelain per gram, although effective, can be irritating to the skin. As used herein, the term "about" is intended to encompass the recited value, plus or minus 5%.

Thus, the compositions of the invention comprise at least about 60 GDU per gram of bromelain in a dermatologically acceptable carrier. The compositions preferably contain at least about 100 GDU bromelain per gram, and more preferably at least about 150 GDU bromelain per gram. Still more preferably, the compositions contain at least about 200 GDU bromelain per gram. In alternative embodiments, the compositions comprise at least about 250 GDU per gram of bromelain.

In order to minimize burning, itching, or irritation due to excessive concentrations of bromelain, the compositions preferably comprise between 60 and 300 GDU of bromelain per gram, and more preferably between 100 and 300 GDU of bromelain per gram. In other embodiments, the compositions may comprise between 200 and 300 GDU of bromelain per gram, between 60 and 250 GDU of bromelain per gram, or between 100 and 250 GDU of bromelain per gram. Particularly preferred compositions comprise about 180 GDU of bromelain per gram.

For convenience, the preparations of the invention may be prepared based upon quantities of crude bromelain extract. When practicing the invention without a measurement of enzyme activity, it will be understood that the quantities set out below are necessarily approximations, and that the activities of the compositions so produced may vary significantly (e.g., by a factor of two) from those prepared on the basis of GDU per gram. With that caveat, the compositions of the invention preferably comprise between 2% and 10% by weight crude bromelain extract, and more preferably between 3% and 10% by weight crude bromelain extract. In other embodiments, the compositions may comprise between 6% and 10% by weight crude bromelain extract, between 2% and 7.5% by weight crude bromelain extract, or between 3% and 7.5% by weight crude bromelain extract. Particularly preferred compositions comprise about 5% by weight crude bromelain extract.

Preferably, the bromelain component of the compositions of the invention is a crude bromelain extract from pineapple fruit, core and/or stem, in which the protein components have not been fractionated or otherwise separated. Examples of crude bromelain extract include, but are not limited to, acetone-, ethanol- and ammonium salt-precipitated powders, filtered and lyophilized plant juices, reverse micellar extracts, and other crude protein isolates prepared by methods known in the art of protein extraction. In these embodiments of the invention, the bromelain compositions contain an array of protease enzymes, as well as natural levels of phosphatase and peroxidase activity, and a complement of protease inhibitors.

The dermatologically acceptable carrier is preferably a cream or lotion. Preferred compositions according to the present invention may comprise an emulsified mixture of water, plant-based fatty acids, triglycerides, emulsifiers, citric acid, potassium sorbate and bromelain.

As used herein, the term "dermatologically acceptable carrier" refers to vehicles, diluents, and carriers known in the art to be suitable for use in dermatological compositions. A dermatologically acceptable carrier can further include adjuvants, additives, and excipients that enhance the carrier's structure and function, including but not limited to buffers, preservatives, gelling agents, rheological modifiers and stabilizers, moisturizers, and humectants. Suitable components are those known in the art to be suitable for use in contact with the skin of humans without undue toxicity, irritation, or allergic response. Suitable materials may be selected from the "Inventory of ingredients employed in cosmetic products," provided in European Commission Decision 2006/257/EC of Feb. 9, 2006. The dermatologically acceptable carrier may take the physical form of a liquid, lotion, cream, butter, gel or ointment. Water-containing emulsions, in the form of lotions or creams, are preferred carriers, as they permit an effective amount of the composition to be applied to the area of skin in need of treatment, do not rapidly dry out, and maintain contact of the skin with the bromelain for an extended period of time. By moisturizing and softening the stratum corneum, lotions and creams also improve the rate of penetration of bromelain into the epidermis.

Lotion and cream compositions according to the invention contain water, which may be present in amounts ranging from about 20% to about 85% by weight, and an effective amount of an emulsifier, typically from about 2% to about 10% by weight. Preferably, the water is present at 30-75%, and more preferably at 40-60% by weight. The compositions preferably contain a dermatologically acceptable oil, which may be present at between 1% and 20%, preferably between 5% and 15% by weight. Suitable oils are well known in the cosmetic arts, and include but are not limited to grapeseed oil, olive oil, sweet almond oil, avocado oil, sesame oil, canola oil, jojoba oil, and the like, as well as mineral oil and synthetic oils such as dimethicone. The compositions preferably contain a semisolid triglyceride, including but not limited to shea butter, cocoa butter, illipe butter, mango butter, avocado butter or the like, in amounts ranging from about 1% to about 20%, preferably between about 4% and about 15%. A stiffener, such as stearic acid or 12-hydroxystearic acid, may be present, preferably in amounts ranging from 1% to 15%, and preferably between 4% and 10%; the amount may be varied depending on whether a lotion or cream is desired.

Preferably, an emulsifier, such as one or more of emulsifying wax NF, glyceryl stearate, cetearyl alcohol, or sodium stearoyl lactylate, is present in the composition in order to uniformly incorporate water into the ointment. The amount of water may range from about 1% to about 25% by weight, and the emulsion is preferably of the water-in-oil type.

Humectants, including but not limited to glycerin, sugar alcohols, or aloe vera gel, may be present at between 0.5% and 5% by weight. An effective amount, typically 0.4 to 0.8 percent by weight, of one or more preservatives, including but not limited to potassium sorbate, citric acid, propylparaben, methylparaben, diazolidinyl urea, and imidazolidinyl urea, may be present.

Ointment compositions may include any of the oils and triglycerides above, and may further comprise a hydrocarbon base such as hard paraffin, soft paraffin, microcrystalline wax, or ceresin wax. Non-hydrocarbon bases such as wool fat or beeswax may also be employed.

When the composition is a lotion, cream or ointment, it is preferable to prepare a base carrier (the "cosmetically acceptable topical carrier") and then add the appropriate weight percent of bromelain at a temperature below 25° C. A representative range of formulations of a topical carrier, suitable for use in the present invention, is set out in Table 1:

TABLE 1

A Cosmetically Acceptable Topical Carrier

| Ingredient | % w/w |
| --- | --- |
| Shea Butter | 4%-11% |
| Grapeseed Oil | 8%-12% |
| ECOMulse ™ | 6%-8% |
| Stearic Acid | 4%-10% |
| Citric Acid | 0.4% |
| Potassium Sorbate | 0.4% |
| Distilled water | (q.s. to 100%) |

EXAMPLES

A cosmetically acceptable topical carrier was prepared by combining distilled water (1575 mL), glycerin (72 g), citric acid (8 g) and potassium sorbate (14 g) in a container and heating this mixture to 70° C. In a separate container, shea butter (45 g), grapeseed oil (240 g), ECOMulse™ (a blend of glyceryl stearate, cetearyl alcohol, and sodium stearoyl lactylate, 174 g) and stearic acid (34 g) were combined and heated to 70° C. The containers were held at 70° C. for 20 minutes. The contents of the two containers were then combined and mixed, and the resulting emulsion was stirred while being allowed to cool to 25° C., resulting in a thick lotion.

The topical carrier thus prepared was combined with a bromelain-maltodextrin powder (381 g) and mixed until homogeneous. The powder used in this example was a product of JRBB Nutrition, distributed by Innate Source Inc., Greeley, Colo., containing 35% bromelain acetone powder by weight (about 333 micrograms of enzyme/g of powder), which assayed at 1200 GDU/g. The resulting composition contained 180 GDU/g bromelain.

Thirty human subjects were recruited, who voluntarily applied the above-described composition to healthy skin and self-reported on the results obtained. After four weeks of three-times-daily application, 100% of subjects reported no redness, itching, burning, or dryness.

Thirty-five human subjects having a variety of skin diseases or syndromes were then recruited, to voluntarily apply the composition to affected skin and self-report on the results obtained. Subjects applied the composition as needed to obtain satisfactory relief; the frequency of application ranged from once daily to four times daily. Subjects reported on any relief obtained, any side effects, and how well the composition performed relative to topical agents previously tried. The results are presented in Table 2:

TABLE 2

Results of Treatment

| Condition | Area(s) Treated | Frequency of Application | Relief Obtained | Time to relief (Min) | Days used | Side Effects | Other Products | Relative Performance |
| --- | --- | --- | --- | --- | --- | --- | --- | --- |
| Allergy | Legs, Arms, Chest, Other | When Needed | Yes | 2 | 300 | None | Udder Cream ™, Workman's Hands ™, Aloe, Corticone Cream | Significantly Better |
| | | When Needed | Yes | 7 | 120 | None | | |
| | Back, Neck | When Needed | Yes | 1 | 180 | None | Sarna ™ | Somewhat Better |
| | Legs, Arms, Neck, Back | When Needed | Yes | 3 | 400 | None | Calamine Lotion, Hydrocorticone Anti-Itch | Significantly Better |
| | Legs, Arms, Neck, Back, Chest | When Needed | Yes | 15 | 450 | None | Dermalogica Barrier Repair ™ | Somewhat Better |
| Burns | Arms | When Needed | Yes | 2 | 300 | None | Udder Cream ™, Workman's Hands ™, Aloe, Corticone Cream | Significantly Better |
| | Legs, Arms, Neck, Back | When Needed | Yes | 3 | 400 | None | Calamine Lotion, Hydrocorticone Anti-Itch | Significantly Better |
| | Legs, Arms, Neck, Back, Chest | When Needed | Yes | 15 | 450 | None | Benadryl ™ | Somewhat Better |

TABLE 2-continued

Results of Treatment

| Condition | Area(s) Treated | Frequency of Application | Relief Obtained | Time to relief (Min) | Days used | Side Effects | Other Products | Relative Performance |
|---|---|---|---|---|---|---|---|---|
| | Legs, Arms, Chest | When Needed | Yes | 1 | 210 | None | Cortaid ™, Aloe Gel, Benadryl ™ Cream | Significantly Better |
| Contact Dermatitis | Hands | 1× Daily | Yes | 5 | 20 | None | Benadryl ™ | Significantly Better |
| | Legs, Arms, Neck, Back, Chest | When Needed | Yes | 20 | 450 | None | Cortisone | Significantly Better |
| | Legs, Arms, Back, Chest | When Needed | Yes | 1 | 450 | None | Cortisone, Benadryl ™ | Significantly Better |
| | Legs, Arms | When Needed | Yes | 3 | 300 | None | Cortisone, Benadryl ™ | Significantly Better |
| | Legs, Arms, Neck | When Needed | Yes | 15 | 400 | None | Cortisone | Significantly Better |
| Cracked Finger Tips | Hands | 2× Daily | Yes | | 400 | None | None | |
| | Hands | 4× Daily | Yes | | 28 | None | None | |
| | Hands | 3× Daily | Yes | 7 | 120 | None | | |
| Diabetic Itch | Legs, Arms, Chest | 2× Daily | Yes | 1 | 300 | None | Lac-Hydrin ™ | Somewhat Better |
| Eczema | Back | 1× Daily | Yes | 1 | 200 | None | None | |
| | Legs, Arms, Neck, Back, Chest | When Needed | Yes | 20 | 450 | None | Cortisone | Significantly Better |
| | Legs, Arms, Chest | 2× Daily | Yes | 1 | 210 | None | Cortaid ™, Aloe Gel, Benadryl ™ Cream | Significantly Better |
| | Back | 1× Daily | Yes | 1 | 330 | None | CVS Anti-Itch Lotion, Benadryl ™ | Somewhat Better |
| | | 2× Daily | Yes | NA | Intermittent | None | | |
| | Arms, Legs, Other | 1× Daily | Yes | 4 | 180 | None | Vaseline Total Moisture ™, Lubriderm ™ | Significantly Better |
| | Feet and Ankles | 1× Daily | Yes | 1 | 10 | None | Sarna ™ | Significantly Better |
| | Back | 1× Daily | Yes | 1 | 200 | None | None | |
| Idiopathic Itch | Back | 1× Daily | Yes | 1 | 330 | None | CVS Anti-Itch Lotion, Benadryl ™ | Somewhat Better |
| | Arms, Legs | When Needed | Yes | 2 | 300 | None | Benadryl ™ | Significantly Better |
| | Legs, Arms, Neck, Back, Chest | 2× Daily | Yes | 15 | 450 | None | Dermalogica Barrier Repair ™ | Somewhat Better |
| | Legs, Arms | When Needed | Yes | 60 | 320 | None | BioFreez ™ | Significantly Better |
| | Legs, Arms | 2× Daily | Yes | 5 | 150 | None | Cortisone | Significantly Better |
| | Legs, Arms, Neck, Back | When Needed | Yes | 3 | 400 | None | Calamine Lotion, Hydrocorticone Anti-Itch | Significantly Better |
| | Legs, Arms, Back, Chest | 1× Daily | Yes | 1 | 450 | None | Cortisone, Benadryl ™ | Significantly Better |
| | Back | 1× Daily | Yes | 5 | 400 | None | Sarna ™ anti-itch lotion, Aveeno ™; Eucerin Intensive Repair ™ | Significantly Better |
| | Legs, Back | 1× Daily | Yes | 1 | 100 | None | | |
| Itch of a healing Incision | Stomach | 1× Daily | Yes | 1 | 40 | None | None | |
| Insect Bites | Legs, Arms | When Needed | Yes | 5 | 60 | None | Cortisone, Aloe | Significantly Better |
| | Legs, Arms, Chest | When Needed | Yes | 1 | 210 | None | Cortaid ™, Aloe Gel, Benadryl ™ Cream | Significantly Better |
| | Arms, Legs, Other | When Needed | Yes | 4 | 180 | None | Vaseline Total Moisture ™, Lubriderm ™ | Significantly Better |
| | Legs, Arms, Neck, Back, Chest | When Needed | Yes | 20 | 450 | None | Cortisone | Significantly Better |
| | Back | When Needed | Yes | 1 | Intermittent | None | | |
| | Legs, Arms | When Needed | Yes | 60 | 320 | None | BioFreez ™ | Significantly Better |
| | Legs, Arms, Back, Chest | When Needed | Yes | 1 | 450 | None | Cortisone, Benadryl ™ | Significantly Better |

TABLE 2-continued

Results of Treatment

| Condition | Area(s) Treated | Frequency of Application | Relief Obtained | Time to relief (Min) | Days used | Side Effects | Other Products | Relative Performance |
|---|---|---|---|---|---|---|---|---|
| | Legs, Arms | When Needed | Yes | 3 | 300 | None | Cortisone, Benadryl ™ | Significantly Better |
| | Arms, Legs | When Needed | Yes | 2 | 300 | None | Benadryl ™ | Significantly Better |
| | Back, Neck | When Needed | Yes | 1 | 180 | None | Sarna ™ | Somewhat Better |
| | Legs, Arms, Neck, Back | When Needed | Yes | 3 | 400 | None | Calamine Lotion, Hydrocorticone Anti-Itch | Significantly Better |
| | Legs, Arms, Chest, Other | When Needed | Yes | 2 | 300 | None | Udder Cream ™, Workman's Hands ™, Aloe, Corticone Cream | Significantly Better |
| | Legs, Arms, Neck | When Needed | Yes | 15 | 400 | None | Cortisone | Significantly Better |
| | Legs, Arms, Back, Forehead | When Needed | Yes | 1 | 330 | None | CVS Anti-Itch Lotion, Benadryl ™ | Somewhat Better |
| | Legs | When Needed | Yes | 1 | Intermittent | None | | |
| | Legs, Arms, Neck, Back, Chest | When Needed | Yes | 15 | 450 | None | Benadryl ™ | Somewhat Better |
| Jellyfish Sting | Arms, Legs | When Needed | Yes | 2 | 300 | None | Benadryl ™ | Significantly Better |
| Joint Pain | Legs, Arms | 2× Daily | No | N/A | 400 | None | None | |
| Psoriasis | | When Needed | Yes | 7 | 120 | None | | |
| | Arms, Legs, Other | 1× Daily | Yes | 4 | 180 | None | Vaseline Total Moisture ™, Lubriderm ™ | Significantly Better |
| | Arms, Legs | 1× Daily | Yes | 1 | 20 | None | Cortisone | Same |
| | Legs, Arms, Neck, Back, Chest | When Needed | Yes | 20 | 450 | None | Cortisone | Significantly Better |
| Rash | Legs, Arms, Chest, Other | When Needed | Yes | 2 | 300 | None | Udder Cream ™, Workman's Hands ™, Aloe, Corticone Cream | Significantly Better |
| | Legs, Arms, Neck, Back, Chest | When Needed | Yes | 15 | 450 | None | Dermalogica Barrier Repair ™ | Somewhat Better |
| | Legs, Arms, Neck, Back | When Needed | Yes | 3 | 400 | None | Calamine Lotion, Hydrocorticone Anti-Itch | Significantly Better |
| | Legs, Arms, Neck | When Needed | Yes | 15 | 400 | None | Cortisone | Significantly Better |
| | Legs, Arms, Neck, Back, Chest | When Needed | Yes | 20 | 450 | None | Cortisone | Significantly Better |
| | Legs, Arms, Chest | When Needed | Yes | 1 | 210 | None | Cortaid ™, Aloe Gel, Benadryl ™ Cream | Significantly Better |
| | Legs, Arms, Back, Chest | When Needed | Yes | 1 | 450 | None | Cortisone, Benadryl ™ | Significantly Better |
| | Legs, Arms | When Needed | Yes | 3 | 300 | None | Cortisone, Benadryl ™ | Significantly Better |
| Rosacea | Face | 2× Daily | Yes | NA | 450 | None | Metronidazole and Tetracycline | Significantly Better |
| | Face | 2× Daily | Yes | NA | 90 | None | Metronidazole and Tetracycline | Significantly Better |
| | Face | 2× Daily | Yes | NA | Intermittent | None | Metronidazole and Tetracycline | Significantly Better |
| | Face | 2× Daily | Yes | NA | 90 | None | Metronidazole and Tetracycline | Significantly Better |
| Shingles | Legs | 3× Daily | Yes | | Intermittent | None | Metronidazole and Tetracycline | Significantly Better |
| Sun Burn | Arms, Legs, Face, Back | When Needed | Yes | 2 | Intermittent | None | Benadryl ™ | Significantly Better |
| | Arms, Legs, Face, Back | When Needed | Yes | 2 | Intermittent | None | Benadryl ™ | Significantly Better |

In view of the results obtained, the invention provides a method of relieving itch, inflammation, irritation, and dryness-associated fissures (cracking) of the skin, comprising the topical administration of an effective amount of a bromelain-containing composition of the invention. Several of the experimental subjects also reported a general improvement in the health, color, texture, and cosmetic appearance of their skin, which was significant enough to be commented upon by third parties. The invention more particularly provides a method relieving the symptoms of allergy, burns, contact dermatitis, eczema, cracked fingertips, idiopathic itch, diabetic itch, itch associated with wound healing, insect bites, jellyfish stings, psoriasis, rash, rosacea, shingles, or sunburn, which comprises the topical administration of an effective amount of a bromelain-containing composition of the invention. An effective amount is an amount sufficient to coat the affected area of the skin with a layer of the composition, and will ordinarily be between 0.05 and 1.0 grams per square inch of skin.

Bromelain works by an unknown mechanism to reduce the redness and itching associated with skin irritation caused by a variety of sources. The utility of the invention is not limited to the treatment of insect bites and stings, but appears to include a broad class of itch-associated conditions. The compositions of the invention are expected to be effective for treating psoriasis, rosacea, skin allergies, winter itch, chronic itch, cracked fingertips, eczema (atopic and allergic dermatitis), and other forms of chronic or idiopathic itching, and the itch associated with diabetes and wound healing. Without wishing to be bound by theory, the inventor suggests that bromelain may selectively and rapidly cleave endogenous pro-inflammatory peptides that are over-expressed as a part of the inflammatory response to irritants, and in conditions such as dermatitis, rosacea and psoriasis, and that this, in turn, reduces the erythema, swelling and itching that are associated with these conditions.

The benefits of formulating the active ingredient into a lotion, cream, or ointment are a substantially improved method of application, the ability to keep the active ingredient at the site of injury and the replenishment of natural moisture to the skin, thereby accelerating healing. In preferred embodiments, the use of a limited number of non-allergenic ingredients in a cosmetically acceptable topical carrier decreases the chance of an allergic reaction to the lotion.

The foregoing detailed description has been directed to a particular embodiment of the invention, for the purposes of illustration and explanation. It will be apparent to those skilled in the art that there are obvious modifications and changes in the compositions and processes set forth, the practice of which will not depart from the scope of the appended claims or the spirit of the invention.

I claim:

1. A method of relieving the symptoms of rosacea, comprising the topical administration, to skin affected by rosacea, of an effective amount of a topical composition comprising either:
    (a) between 60 and 300 GDU (gelatin dissolving units) of bromelain per gram; or
    (b) between 2% and 10% by weight crude bromelain extract;
in a dermatologically acceptable carrier.

2. The method according to claim 1, wherein the composition comprises either:
    (a) between 100 and 300 GDU of bromelain per gram; or
    (b) between 3% and 10% by weight crude bromelain extract.

3. The method according to claim 2, wherein the composition comprises either:
    (a) between 200 and 300 GDU of bromelain per gram; or
    (b) between 6% and 10% by weight crude bromelain extract.

4. The method according to claim 3, wherein the composition comprises either:
    (a) between 250 and 300 GDU of bromelain per gram; or
    (b) between 7.5% and 10% by weight crude bromelain extract.

5. The method according to claim 4, wherein the composition comprises either:
    (a) about 300 GDU of bromelain per gram; or
    (b) about 10% by weight crude bromelain extract.

6. The method according to claim 1, wherein the composition comprises either:
    (a) between 100 and 250 GDU of bromelain per gram; or
    (b) between 3% and 7.5% by weight crude bromelain extract.

7. The method according to claim 6, wherein the composition comprises either:
    (a) about 180 GDU of bromelain per gram; or
    (b) about 5% by weight crude bromelain extract.

8. The method according to claim 7, wherein the dermatologically acceptable carrier is a cream or lotion.

9. The method according to claim 7, wherein the dermatologically acceptable carrier comprises one or more carrier oils selected from the group consisting of grapeseed oil, rice bran oil, sunflower oil, olive oil, soy oil, coconut oil and combinations thereof, in an amount that ranges from 8 to 12 weight percent.

10. The method according to claim 7, wherein the dermatologically acceptable carrier comprises one or more skin softening agents selected from the group consisting of Shea butter, avocado butter, cocoa butter, illipe butter, mango butter and combinations thereof, in (Original) an amount that ranges from 4 to 1 weight percent.

11. The method according to claim 7, wherein the dermatologically acceptable carrier comprises one or more emulsifiers selected from the group consisting of emulsifying wax NF, glyceryl stearate, cetearyl alcohol, sodium stearoyl lactylate, and combinations thereof, in an amount that ranges from 6 to 8 weight percent.

12. The method according to claim 6, wherein the dermatologically acceptable carrier is a cream or lotion.

13. The method according to claim 6, wherein the dermatologically acceptable carrier comprises one or more carrier oils selected from the group consisting of grapeseed oil, rice bran oil, sunflower oil, olive oil, soy oil, coconut oil and combinations thereof, in an amount that ranges from 8 to 12 weight percent.

14. The method according to claim 6, wherein the dermatologically acceptable carrier comprises one or more skin softening agents selected from the group consisting of Shea butter, avocado butter, cocoa butter, illipe butter, mango butter and combinations thereof, in an amount that ranges from 4 to 1 weight percent.

15. The method according to claim 6, wherein the dermatologically acceptable carrier comprises one or more emulsifiers selected from the group consisting of emulsifying wax NF, glyceryl stearate, cetearyl alcohol, sodium stearoyl lactylate, and combinations thereof, in an amount that ranges from 6 to 8 weight percent.

16. The method according to claim 1, wherein the dermatologically acceptable carrier is a cream or lotion.

17. The method according to claim 1, wherein the dermatologically acceptable carrier comprises one or more carrier oils selected from the group consisting of grapeseed oil, rice bran oil, sunflower oil, olive oil, soy oil, coconut oil and combinations thereof, in an amount that ranges from 8 to 12 weight percent.

18. The method according to claim 1, wherein the dermatologically acceptable carrier comprises one or more skin softening agents selected from the group consisting of Shea butter, avocado butter, cocoa butter, illipe butter, mango butter and combinations thereof, in an amount that ranges from 4 to 1 weight percent.

19. The method according to claim 1, wherein the dermatologically acceptable carrier comprises one or more emulsifiers selected from the group consisting of emulsifying wax NF, glyceryl stearate, cetearyl alcohol, sodium stearoyl lactylate, and combinations thereof, in an amount that ranges from 6 to 8 weight percent.

\* \* \* \* \*